United States Patent [19]

Compagnucci et al.

[11] Patent Number: 5,154,698
[45] Date of Patent: Oct. 13, 1992

[54] SINGLE USE SYRINGE INCORPORATING A SLIDING PROTECTION CAP FOR THE NEEDLE

[76] Inventors: Patrizio Compagnucci, Via Alfieri, 17; Massimo Giuliani, Via del Tesoro, 37, both of Falconara (AN), Italy

[21] Appl. No.: 777,664

[22] Filed: Oct. 15, 1991

[30] Foreign Application Priority Data

Oct. 19, 1990 [IT] Italy .................................. 592/90[U]
Apr. 19, 1991 [IT] Italy ......................... AN91A000010

[51] Int. Cl.5 .............................................. A61M 5/00
[52] U.S. Cl. .................................... 604/110; 604/198; 604/263
[58] Field of Search ............... 604/198, 195, 192, 187, 604/263, 199, 110

[56] References Cited

U.S. PATENT DOCUMENTS

| 4,392,859 | 7/1983 | Dent ..................................... 604/198 |
| 4,923,445 | 5/1990 | Ryan ............................... 604/198 X |
| 4,969,877 | 11/1990 | Kornberg ......................... 604/198 X |

Primary Examiner—John D. Yasko
Attorney, Agent, or Firm—Leonard Bloom

[57] ABSTRACT

This invention concerns a single-use syringe having an external longitudinally sliding conforming protection cap for the needle. The sliding cap and the syringe have a mechanism for reciprocal coupling, whose interference determines the forward and backward end of stroke stop of the cap along the syringe.

3 Claims, 3 Drawing Sheets

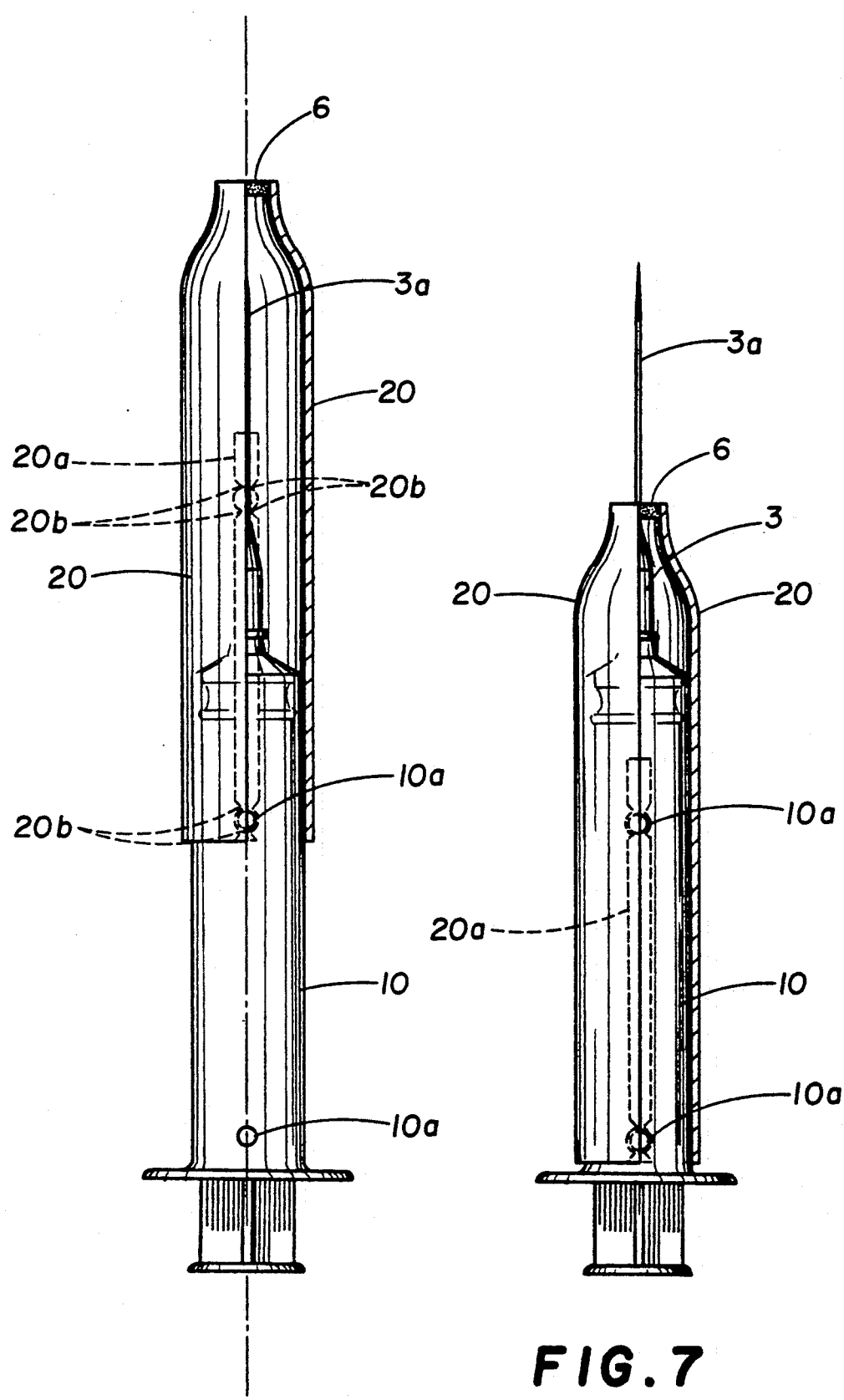

SINGLE USE SYRINGE INCORPORATING A SLIDING PROTECTION CAP FOR THE NEEDLE

This invention concerns a single-use syringe having a sliding protection cap to prevent users from pricking themselves accidentally with the needle of the syringe. The object in question was designed to ensure maximum utilization hygiene and safety in the use of plastic "non reusable-throw away" syringes which are the syringes most commonly used in the home, surgeries and hospitals.

In particular, the protection cap of the syringe according to the invention was designed expressly to prevent users from pricking themselves with the needle of a syringe after use, which—as is commonly known—can be an extremely dangerous source of infection and contamination of illnesses, some of which can be mortal.

This feature is especially useful if considered in relation to the current precarious methods of using single-use syringes: currently these syringes are sold—inside a sterile and sealed package—with a very thin removable cap which covers the length of the metal needle and press fits, into the collar of the syringe at the base of the needle. This cap must be removed before giving the injection, but it should also be replaced after the syringe has been used and before it is thrown away.

It should be noted however, that the action required to refit the very small cap on the needle—which should always be done to avoid throwing away the syringe in the garbage with the dangerous needle uncovered—is extremely risky for the person carrying out the operation in that the protection cap is very small.

In fact, often, the person who is carrying out this operation, does not manage—especially if he is distracted—to fit the needle immediately into the hole in the cap: in this case the needle is therefore pushed forward just outside the cap with a good chance of dangerously pricking—often quite deeply—the fingers of the hand holding the cap.

As previously mentioned—the new syringe according to the invention was expressly designed to eliminate any risk of accidental needle pricks to those using single-type syringes.

The idea behind the invention was to fit the syringe with a cap having a wide cross-section and consistent length, which does not fit into the base of the needle collar, but couples and slides with the external walls of the syringe, so that when the cap is completely pushed out with respect to the front end of the syringe, it protects the needle, while when it is pushed completely back, it allows the needle to project externally through a slot at the centre, which the cap has for this purpose, on its front end.

From this brief description it is easy to understand how safe and rational the use of a syringe having the above sliding cap will be.

In fact, while the syringe is still in its sterile package, the cap is held in a fully forward position, so as to cover the needle entirely; when the syringe is to be used, the above cap is pushed backwards—along the external sides of the syringe; when the syringe has been used and is ready to be thrown away, the cap will be pushed forward to cover the needle completely.

It is obvious therefore that the action carried out to cover the needle is carried out in total safety since in this situation the fingers of the user push the sliding cap from the back of the needle and the fingers of the user and the needle never move dangerously against each other, as in the case of current syringes fitted with the small removable caps.

Another purpose of the invention is to prevent the risk of needle pricks when the needle is pulled out of the syringe in order to transfer blood from test tubes.

In certain cases, for example in test laboratories, after having taken the blood sample, the needle must be removed from the syringe in order to transfer the blood from the syringe into one or several test tubes.

In this case, the above cap which slides outside the syringe, is of no particular help or prevention against the above type of accident since the removal of the needle requires the complete removal of the cap from the syringe in order to hold the collar of the needle support fitted on the front opening of the syringe, between the thumb and forefinger.

The user therefore finds himself in a dangerous situation during which he has to work with a used syringe with an uncovered needle, where an accidental needle prick could be a dangerous source of infection and contamination of illnesses, some of which can be mortal.

Consequently, a solution that would allow the removal of the needle while it was still inside the sliding cap, was investigated; a solution was found whereby the sliding cap can be removed from the body of the syringe while disconnecting the support needle collar at the same time, thanks to the special shape of this collar which is connected by suitable a connection mechanism inside the opening of the sliding cap.

In the preferred embodiment of the invention, this sliding cap has an opening with a number of longitudinal slits which separate an annular series of elastic tabs, each of which terminates with an internal raised edge having a semi-circular cross-section that is oriented towards the body of the syringe which press fits at the end of the forward or backward run of the cap along the syringe, within two annular grooves having a semi-circular cross-section on the external surface of the syringe, one close to the tip and the other close to the opening (plunger opening).

The support collar (needle end) of the chamber for carrying the needle is at the centre of a bell-shaped bell-shaped chamber having an ogival profile whose lateral external surface perfectly connects and fits to the cylindrical surface of the body of the syringe.

At the base of this bell-shaped chamber there is an annular groove having a semicircular cross-section, similar to the pair of grooves close to the two ends of the syringe, so that when the cap of the syringe is moved forward past the annular groove that is formed close to the tip of the syringe, the elastic teeth positioned at the opening can wedge into place—after having slipped over the groove close to the tip of the syringe—in the groove on the bell-shaped chamber which incorporates the support collar of the needle.

By holding and closing the cap at the opening it hooks securely to the bell-shaped chamber thanks to the above teeth, so that when the cap is removed completely from the syringe, the needle-holder collar is also removed from the press fit opening at the top of the syringe with the protective cover covering the needle, such that the needle may be disposed with the protective cap positioned thereover while the body of the syringe is retained for further use if so desired.

At this point the needle can be thrown away with no danger whatsoever since it is covered by the above cap in which it is fixed and enclosed.

According to another embodiment of the invention, the stop of the cap on the syringe and/or on the bell-shaped chamber incorporating the support collar of the needle can be obtained with a nut which is screwed outside the opening of the cap and which bends the elastic tabs on the opening of the cap, inwards, until the cap stops.

For major clarity the description of the invention continues with reference to the drawings which are intended for illustrative purposes and not in a limiting sense, in which.

The use of a special support collar of the needle provides the user with the double protection described above. If the second protection is not required, namely that offered when the needle is removed, the syringe in question will have a standard support collar for the needle, as shown in the embodiment illustrated in FIGS. 5, 6 and 7.

Figures 1, 2, 3:
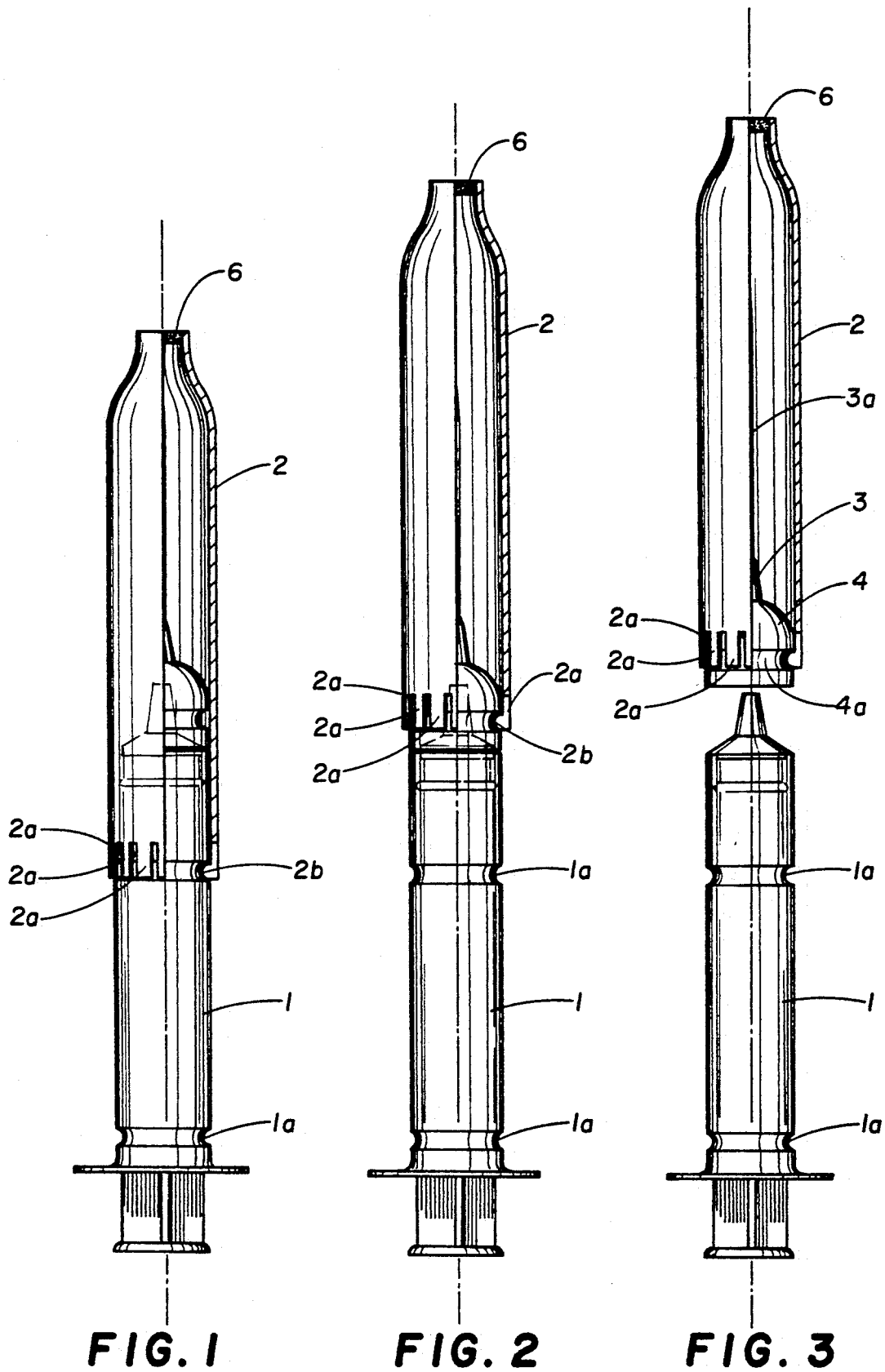
FIG. 1 shows the syringe according to the invention, represented with a half view and a half cross-section, with the protection cap pulled out in full to cover the needle.
FIG. 2 shows the syringe according to the invention, represented with a half view and a half cross-section with the protection cap removed from the body of the syringe but still hooked to the support collar of the needle.
FIG. 3 shows the syringe according to the invention, represented in a half view and in a half cross-section, with the support collar of the needle removed from the syringe and hooked inside the protection cap.
Figure 5:
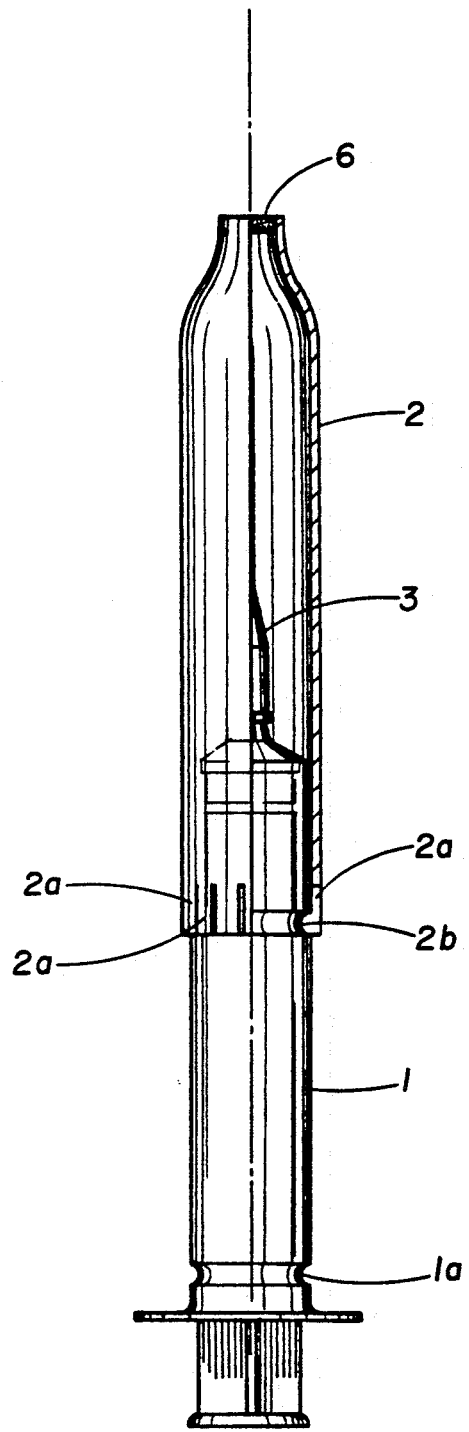

FIG. 5 shows the syringe of FIG. 1 in half a view and in half a cross-section, with a standard support collar for the needle;

FIGS. 6 and 7 show a further construction embodiment of the syringe according to the invention.

The features of the present invention are, as is seen in the drawings, used in single-use syringes of the type having a hollow body in which the substance to be administered is received and maintained and a hole that is formed in the body wherein the substance to be administered passes during movement of a plunger inside the hollow body via a plunger opening that is formed in the body opposite the hole.

With reference to FIGS. 1, 2 and 3, the syringe (1) has two external annular groves (1a) having a semi-circular cross-section, one close to its tip and the other close to its opening.

Outside the syringe (1) there is cylindrical sliding cap (2) having an opening with a number of longitudinal slits which separate an annular series of elastic tabs (2a), each of which terminates with an internal raised edge (2b) having a semi-circular cross-section, which press fits, at the end of the backward or forward run of the cap (2) onto the syringe (1) into the above annular grooves (1a) which therefore act as end housings and end of run stops for the cap (2).

The support collar (3) of the needle (3a) is made in a bell-shaped chamber (4) having an ogival shape, whose external surface fits perfectly with the cylindrical surface of the body of the syringe (1).

At the base of the bell-shaped chamber (4) there is an external annular groove (4a) having a semi-circular cross-section identical to the grooves of the syringe (1).

As illustrated in FIG. 3, by completely removing the cap (2) from the syringe (1), during the forward run of the cap, the internal edge (2b) of the elastic tabs (2a) couples with the annular groove (4a), with consequent engagement of the bell-shaped chamber (4) which is wedged in the opening of the cap (2).

The collar (3) can therefore be removed from the opening of the syringe (1) with the needle (3a) covered and enclosed inside the cap (2); in holding the cap by its opening, the connection with the bell-shaped chamber (4), is strengthened and stabilized, so that the same is fastened to the cap (2) and is removed from the syringe (1) together with the cap.

Figure 4:
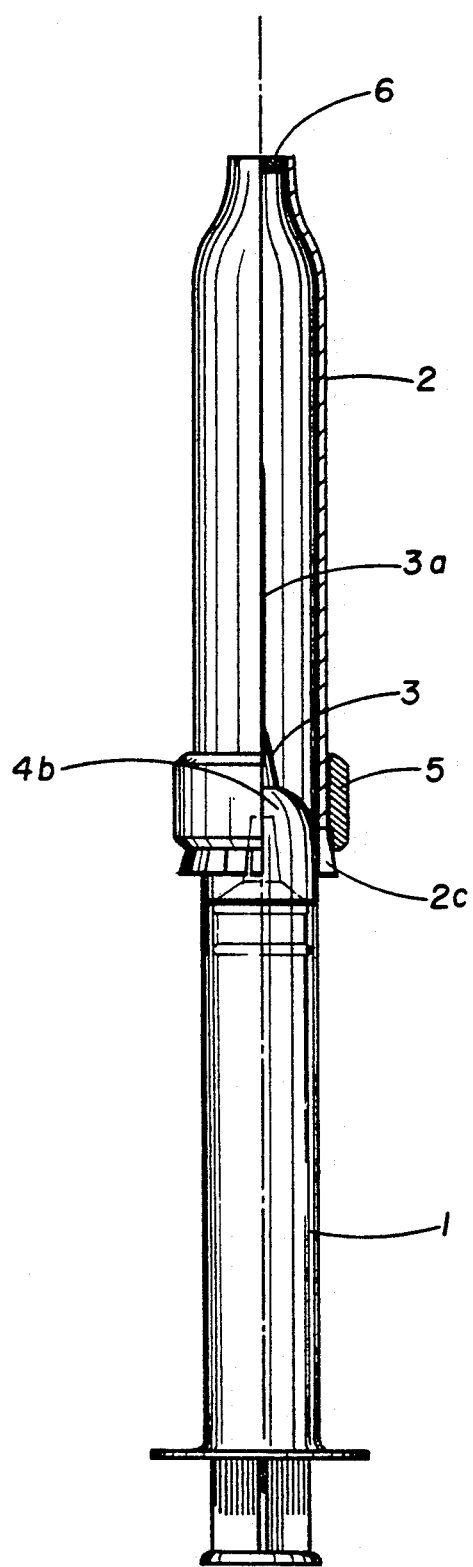
FIG. 4 shows the syringe according to the invention in a further construction embodiment having a fixing nut to stop the sliding cap.

With reference to FIG. 4, it should be noted that in a further construction embodiment of the invention, the cap (2) is fitted with a nut (5) which is screwed outside its opening, thereby creating a gradual hold of the elastic tabs (2c), whose external profile is suitable slanted for this purpose in order to interfere with the opening of the nut (5).

In this version, the elastic tabs do not have any raised internal edge, and the syringe (1) and the bell-shaped chamber (4b) does not have annular grooves for hooking the elastic tabs, since the cap (2) is not stopped by the male and female coupling of adjacent elements, but simply by adherence on the external surface of the syringe (1) or of the bell-shaped chamber (4b) of the tabs (2c) which are gradually fixed by the nut (5) as it is screwed.

With reference to FIGS. 6 and 7, a further embodiment of the syringe according to the invention is described involving the use of a standard support collar (3) for the needle, as in the case of the syringe model illustrated in FIG. 5, which is no more than the syringe illustrated in FIG. 1 without the special ogival bell-shaped chamber.

With reference to FIGS. 6 and 7, a cylindrical cap (20) slides longitudinally along the syringe (10), this cap being fitted internally with two diametrically opposite longitudinal grooves (20a), which act as sliding guides for the two pairs of opposing pins (10a) outside the syringe (10), one of which is close to the tip of the syringe and the other close to its opening.

In order to stop the sliding cap (20) securely at the two possible end of run positions, each groove (20a) of the cap (20) has, in each of its opposite end sections, a stopping housing for the above pins (10a) consisting of two opposing consecutive jaws, drawn close together (20b) that reduce the cross-section of the groove (20a).

In fact, each pin (10a) of the syringe (10) is sized to slide without appreciable resistance along the respective groove (20a) of the cap (20) while it must be pushed firmly to cross the reduced cross-sections delimited by the pair of opposing jaws (20b).

It is obvious that the two reduced passage cross-sections drawn together prevent the pin (10a) from moving freely out of the respective stop area delimited by the two grooves formed by the pair of opposing jaws (20b); thanks to this feature, the danger of unwanted sliding of the cap (20) with respect to the syringe (10) from one of the two end of run positions, is definitely eliminated.

The cap (2 or 20) has a centre hole at its tip which allows the needle (3a) to move out when the cap in pushed back completely.

In particular, this hole is closed by a spongy membrane (6) soaked with disinfecting and sterilizing substances which hermetically seals the internal compartment of the cap until such time as the syringe is used, but which can be easily crossed by the needle (3a) when it is pushed out, as soon as the cap (2 or 20) is pulled backwards.

To replace the spongy membrane (6), a small removable cap could be used which hermetically closes the hole on the tip of the sliding cap.

We claim:

1. In a single-use syringe of the type having a plunger, a hollow body in which the substance to be administered is received and maintained, the body of the syringe having a hole formed therein and a tip on the body over the hole formed in the body, a needle carried by the tip and through which a substance to be administered may be introduced into and/or administered from the hollow body via the hole thereof, the body of the syringe further having a plunger opening formed therein opposite of the tip through which the plunger is slidably received, so that sliding movement of the plunger draws the substance into and/or administers the substance from the hollow body, a sliding protection cap for selectively covering the needle for preventing accidental contact therewith, the cap being carried on the body of the syringe for longitudinal movement of the cap on the syringe, and a reciprocal coupling mechanism formed between the cap and the body of the syringe whose interference defines the forward and backward limits of the longitudinal movement of the cap along the body of the syringe, the improvement thereupon comprised, in combination, of:

the reciprocal coupling mechanism including the cap having a series of annular elastic tabs formed therein by cutting the opening of the sliding cap, each tab terminating with a raised internal edge having a semi-circular cross-section, the internal edge being oriented towards the body of the syringe, and a pair of annular grooves formed on the body of the syringe, one of the annular grooves being located close to the tip on the body of the syringe and the other of the grooves being located close to the plunger opening of the syringe; and the tip of the syringe including a bell-shaped chamber having an oval shape including a needle end on which the needle is carried and an open base opposite the needle end, the open base of the chamber being sized so as to be received over the hole in the body of the syringe opposite to the plunger opening, and further so as to connect perfectly with the shape of the body of the syringe, the base of the bell-shaped chamber having an external annular groove formed therein being of semi-circular cross-section, so as to be identical to the two annular grooves of the reciprocal coupling mechanism that are close to both the tip and the plunger opening of the body of the syringe, whereby the raised internal edge of the cap may be engaged upon forward longitudinal movement of the cap past the annular groove that is formed close to the tip of the syringe; and the bell-shaped chamber being removably joined to the body of the syringe, whereby the needle, the chamber and the cap may all be simultaneously selectively removed from the remainder of the body of the syringe with the protective cover covering the needle, such that the needle may be disposed with the protective cap positioned thereover while the body of the syringe is retained for further use if so desired.

2. The improvement of claim 1, wherein the base of the bell chamber includes an internal annular ridge formed by the annular groove formed in said base, and further wherein the body of the syringe further includes an annular locking groove formed therein forwardly of the annular groove formed close to the tip of the syringe, such that the internal annular ridge of the bell chamber removably engagingly mates with the annular locking groove formed in the body of the syringe, whereby the bell chamber is removably selectively engaged on the body of the syringe.

3. The improvement of claim 1, wherein the cap has a hole formed therein at a forwardmost end thereof, the hole being sealed by a spongy membrane soaked in sterilizing or disinfecting substances.

* * * * *